(12) United States Patent
Han

(10) Patent No.: US 11,053,130 B2
(45) Date of Patent: Jul. 6, 2021

(54) PROCESS FOR THE CO-PRODUCTION OF METHANOL AND AMMONIA

(71) Applicant: Haldor Topsøe A/S, Kgs. Lyngby (DK)

(72) Inventor: Pat A. Han, Smørum (DK)

(73) Assignee: Haldor Topsoe A/S, Lyngby (DK)

( * ) Notice: Subject to any disclaimer, the term of this patent is extended or adjusted under 35 U.S.C. 154(b) by 0 days.

(21) Appl. No.: 16/622,463

(22) PCT Filed: Jul. 20, 2018

(86) PCT No.: PCT/EP2018/069793
§ 371 (c)(1),
(2) Date: Dec. 13, 2019

(87) PCT Pub. No.: WO2019/020522
PCT Pub. Date: Jan. 31, 2019

(65) Prior Publication Data
US 2020/0156953 A1    May 21, 2020

(30) Foreign Application Priority Data

| Jul. 25, 2017 | (DK) | PA 2017 00425 |
| Sep. 25, 2017 | (DK) | PA 2017 00522 |
| May 28, 2018 | (DK) | PA 2018 00237 |
| Jul. 6, 2018 | (DK) | PA 2018 00345 |
| Jul. 6, 2018 | (DK) | PA 2018 00351 |
| Jul. 6, 2018 | (DK) | PA 2018 00352 |

(51) Int. Cl.
| *C01C 1/04* | (2006.01) |
| *C01B 3/02* | (2006.01) |
| *C01B 3/38* | (2006.01) |
| *C01C 1/02* | (2006.01) |
| *C07C 29/151* | (2006.01) |
| *C25B 1/04* | (2021.01) |

(52) U.S. Cl.
CPC ........... *C01C 1/0488* (2013.01); *C01B 3/025* (2013.01); *C01B 3/382* (2013.01); *C01C 1/024* (2013.01); *C07C 29/1518* (2013.01); *C25B 1/04* (2013.01); *C01B 2203/0216* (2013.01); *C01B 2203/0283* (2013.01); *C01B 2203/046* (2013.01); *C01B 2203/061* (2013.01); *C01B 2203/068* (2013.01)

(58) Field of Classification Search
CPC ... C07C 29/1518; C01C 1/0488; C01C 1/024; C01B 3/025; C01B 3/382; C01B 2203/0216; C01B 2203/0283; C01B 2203/046; C01B 2203/061; C01B 2203/068; C01B 2203/0244; C25B 1/04
See application file for complete search history.

(56) References Cited

U.S. PATENT DOCUMENTS

| 4,479,925 A | 10/1984 | Shires et al. |
| 4,792,441 A | 12/1988 | Wang et al. |
| 2004/0182002 A1 | 9/2004 | Malhotra et al. |
| 2007/0256360 A1 | 11/2007 | Kindig et al. |
| 2009/0165459 A1 | 7/2009 | Henriksen et al. |
| 2009/0314994 A1 | 12/2009 | Filippi et al. |
| 2010/0076097 A1 | 3/2010 | Metz et al. |
| 2012/0091730 A1 | 4/2012 | Stuermer et al. |
| 2012/0100062 A1 | 4/2012 | Nakamura et al. |
| 2013/0072583 A1 | 3/2013 | Koskinen et al. |
| 2013/0345325 A1 | 12/2013 | Lecomte et al. |
| 2014/0357736 A1 | 12/2014 | Dahl |
| 2016/0115405 A1 | 4/2016 | Zubrin et al. |

FOREIGN PATENT DOCUMENTS

| EP | 2 166 064 A1 | 3/2010 |
| EP | 2 192 082 A1 | 6/2010 |
| EP | 2 589 574 A1 | 5/2013 |
| EP | 2 676 924 A1 | 12/2013 |
| EP | 2 805 914 B1 | 9/2017 |
| GB | 2545474 A | 6/2017 |
| KR | 10-2005-0075628 A | 7/2005 |
| WO | WO-2007/049069 A1 | 5/2007 |
| WO | WO 2010/008494 A1 | 1/2010 |
| WO | WO-2011/088981 A1 | 7/2011 |
| WO | WO-2012/084135 A1 | 6/2012 |
| WO | WO 2015/067436 A1 | 5/2015 |
| WO | WO 2015/128456 A1 | 9/2015 |
| WO | WO-2016/008820 A1 | 1/2016 |

*Primary Examiner* — Jafar F Parsa
(74) *Attorney, Agent, or Firm* — Blank Rome LLP

(57) ABSTRACT

A process for the combined preparation of methanol and ammonia based on primary steam reforming a hydrocarbon feed stock and adiabatic secondary reforming with oxygen enriched air from electrolysis of water.

6 Claims, No Drawings

PROCESS FOR THE CO-PRODUCTION OF METHANOL AND AMMONIA

The present invention is directed to the co-production of methanol and ammonia. More particular, the invention is based on electrolysis of water and steam reforming of a gaseous hydrocarbon feed stock in the preparation of a carbon oxide, hydrogen and nitrogen containing synthesis gas, which in a first process stage is subjected to methanol synthesis and in a second process stage to ammonia synthesis.

In the conventional methanol process, synthesis gas is typically prepared in so-called two step reforming process. In the two-step reforming process, a desulfurized hydrocarbon feed stock, usually natural gas, is primary reformed in a fired primary steam methane reformer (SMR) and subsequently in an adiabatic secondary steam reformer by partial oxidation of hydrogen and hydrocarbons and adiabatic steam reforming of residual amounts of hydrocarbons from the partial oxidation step. The adiabatic secondary reformer is operated with essentially pure oxygen for use in the partial oxidation step. The essentially pure oxygen is typically supplied from an Air Separation Unit (ASU).

Alternatively, to the 2-step reforming, stand-alone SMR or stand-alone autothermal reforming can be used to prepare the synthesis gas.

Regardless of whether stand-alone SMR, 2-step reforming, or stand-alone ATR is used, the product gas will comprise hydrogen, carbon monoxide, and carbon dioxide as well as other components normally including methane and steam.

Ammonia synthesis gas is conventionally prepared by subjecting hydrocarbon feed of natural gas or higher hydrocarbons to endothermic steam reforming reactions in a fired tubular steam reformer by contact with a steam reforming catalyst. The primary reformed gas is then fed into an adiabatic secondary reformer, wherein part of hydrogen and residual amounts of hydrocarbons in the primary reformed gas are partial oxidized with oxygen enriched process air in presence of a secondary reforming catalyst. From the secondary reformer, raw synthesis gas containing hydrogen, nitrogen, carbon monoxide and carbon dioxide formed during reaction of the feedstock in the above steam reforming reactions and nitrogen introduced into the gas through addition of air in the secondary reforming step.

Recently, a combination of electrolysis of water for production of hydrogen and air separation for the production of nitrogen has been envisaged for the preparation of ammonia synthesis gas. The thus produced hydrogen and nitrogen are combined in stoichiometric ratios to form synthesis gas for ammonia production. The problem with the combination of electrolysis and air separation is, however, that oxygen is produced as byproduct in both electrolysis and air separation, which has no use in the ammonia synthesis, and can be considered as energy losses.

Current processes for co-production of methanol and ammonia involve generally parallel processes in which a common reforming section is used to generate a synthesis gas which is split in separate parallel streams, one of which is used for methanol synthesis and the other for ammonia synthesis. The co-production of methanol and ammonia can also be conducted sequentially or in series, where the synthesis gas produced in the reforming section is first converted to methanol and the unreacted gas containing carbon oxides and hydrogen is subsequently used for ammonia synthesis. Water gas shift and/or carbon dioxide removal steps of the synthesis gas stream are required depending of the desired ratio of methanol product to ammonia product, thus involving the release of $CO_2$ to the atmosphere and the investment in highly expensive and complicated units for conducting the shift conversion and carbon dioxide removal.

The present invention is based on a combination of primary and secondary steam reforming using oxygen from the electrolysis of water in the partial oxidation of hydrocarbon feed stock in the secondary steam reforming process. Hydrogen from the electrolysis is used to adjust the hydrogen/nitrogen molar ratio in the effluent gas from the methanol synthesis to provide an ammonia synthesis gas approximately to the stoichiometric ratio required for the production of ammonia, as well as additional synthesis gas production.

Compared to prior art methods using electrolysis of water for hydrogen production and air separation for nitrogen production, the oxygen product from electrolysis of water is advantageously used for partial oxidation in the secondary reformer so that the costly and energy intensive ASU is avoided in the method according to the invention.

Thus, this invention is a process for the co-production of methanol and ammonia comprising the steps of (a) providing a hydrocarbon feed stock;

(b) preparing a separate hydrogen stream and a separate oxygen stream by electrolysis of water;

(c) primary steam reforming the hydrocarbon feed stock provided in step (a) to a primary steam reformed gas;

(d) providing process air for use in a secondary reforming step by enriching atmospheric air with the separate oxygen stream from step (b);

(e) secondary reforming the primary steam reformed gas from step (c) with the oxygen enriched air to a process gas stream comprising hydrogen, nitrogen, carbon oxides;

(f) introducing at least part of the separate hydrogen stream from step (b) into the process gas stream obtained in step (e) or optionally into the process gas stream after a shift and/or carbon dioxide removal step;

(g) catalytically converting the carbon oxides and a part of the hydrogen contained in the process gas stream in a once-through methanol synthesis stage and withdrawing an effluent containing methanol and a gas effluent containing un-converted carbon oxides, hydrogen and nitrogen;

(h) purifying the gas effluent from step (g) and obtaining an ammonia synthesis gas containing hydrogen and nitrogen; and (i) catalytically converting the nitrogen and the hydrogen of the ammonia synthesis gas in an ammonia synthesis stage and withdrawing an effluent containing ammonia.

The methanol synthesis in the absence of carbon dioxide is governed by the reaction $CO+2H_2 \leftrightarrows CH_3OH$. In the presence of carbon dioxide, methanol is otherwise also generated according to the reaction $CO_2+3 H_2 \leftrightarrows CH_3OH+H_2O$. As apparent from the latter methanol synthesis reaction a lower molar ratio of $CO/CO_2$ in the synthesis gas for the methanol synthesis requires a larger amount of hydrogen.

Thus, in an embodiment of the invention the amount of hydrogen in the process gas is increased by subjecting at least a part of the process gas stream obtained in step (e) to one or more water gas shift reactions, wherein carbon monoxide is reacted to carbon dioxide and hydrogen according the reaction:

$$CO+H_2O \leftrightarrows CO_2+H_2$$

Ideally, the process gas for the synthesis methanol is a gas containing the highest possible molar ratio of $CO/CO_2$.

Thus, in further an embodiment of the invention at least a part of the carbon dioxide is removed from the process gas stream obtained in step (e) or the water gas shifted process gas stream.

Removal of carbon dioxide can be performed by a physical or chemical method known in the art.

The methanol synthesis stage is preferably conducted by conventional means by passing the process gas at high pressure and temperatures, such as 60-150 bars and 150-300° C. through at least one methanol reactor containing at least one fixed bed of methanol catalyst. A particularly preferred methanol reactor is a fixed bed reactor cooled by a suitable cooling agent such as boiling water, e.g. boiling water reactor (BWR).

To provide the required methanol synthesis pressure, the process gas is compressed by means a compressor arranged in front of the at least one methanol reactor.

Accordingly, the invention enables the operation of the methanol and ammonia synthesis section at similar operating pressures, for instance 130 bars, which implies that the process gas needs only be compressed to synthesis pressure upstream the methanol synthesis step and no further compression is necessary after the methanol synthesis. The hydrogen gas stream from the water electrolysis is introduced into the suction section of a process gas compressor in front of a methanol reactor in an amount to provide a molar ratio of the hydrogen to the nitrogen of 2.7-3.3 in the gaseous effluent from the methanol synthesis.

Prior to the gaseous effluent is passed into the ammonia synthesis loop, the gaseous effluent is preferably purified by removing remaining amounts of carbon monoxide and carbon dioxide, preferably by methanation according to the reactions:

$$CO + 3H_2 \leftrightarrows CH_4 + H_2O; \text{ and}$$

$$CO_2 + 4H_2 \leftrightarrows CH_4 + 2H_2O$$

The purifying step can also be based on cryogenic methods, like the so-called coldbox process, which also can be used for adjustment of the $N_2/H_2$ molar ratio by removing excess of $N_2$.

The advantages of the process according to the invention are essentially less consumption of hydrocarbon feed stock (natural gas) and process air and less emission of CO2 in flue gas from the firing of the primary steam reformer at same production rate of methanol and higher production rate of ammonia compared with the conventional process without electrolysis as summarized in the Comparison Table below.

(c) primary steam reforming the hydrocarbon feed stock provided in step (a) to a primary steam reformed gas;

(d) providing process air for use in a secondary reforming step by enriching atmospheric air with the separate oxygen stream from step (b);

(e) secondary reforming the primary steam reformed gas from step (c) with the oxygen enriched air to a process gas stream comprising hydrogen, nitrogen, carbon oxides;

(f) introducing at least part of the separate hydrogen stream from step (b) into the process gas stream obtained in step (e), or optionally into the process gas stream after a shift and/or carbon dioxide removal step;

(g) catalytically converting the carbon oxides and a part of the hydrogen contained in the process gas stream in a once-through methanol synthesis stage and withdrawing an effluent containing methanol and a gas effluent containing un-converted carbon oxides, hydrogen and nitrogen, wherein the hydrogen prepared by electrolysis of water is introduced into the process gas stream in step (f), prior to the methanol synthesis, by introducing the hydrogen into a suction section of a process gas compressor in an amount to adjust a hydrogen/nitrogen molar ratio in the gas effluent to a stoichiometric ratio of 2.7-3.3 required for production of ammonia;

(h) purifying the gas effluent from step (g) and obtaining an ammonia synthesis gas containing hydrogen and nitrogen; and (i) catalytically converting the nitrogen and the hydrogen of the ammonia synthesis gas in an ammonia synthesis stage and withdrawing an effluent containing ammonia.

2. Process of claim 1, wherein at least a part of the process gas stream from step (e) is subjected one or more water gas shift reactions.

3. Process of claim 1, wherein at least a part of the process gas stream from step (e) is subjected to carbon dioxide removal.

| | | | Comparison Table | | | | |
|---|---|---|---|---|---|---|---|
| Technology for syngas preparation | Natural gas feed consumption (Nm³/h) | Natural gas fuel consumption (Nm³/h) | Air consumption (Nm³h) | CH₃OH production (MTPD) | NH₃ production (MTPD) | Power for electrolysis (MW) | CO₂ in flue gas (Nm³/h) |
| Prior art | 45330 | 15392 | 22387 | 1350 | 415 | 0 | 23104 |
| According to the invention | 43607 | 11531 | 20328 | 1350 | 459 | 74 | 17348 |

The invention claimed is:

1. Process for the co-production of methanol and ammonia comprising the steps of:

(a) providing a hydrocarbon feed stock;

(b) preparing a separate hydrogen stream and a separate oxygen stream by electrolysis of water;

4. Process of claim 1, wherein the purifying of the gas effluent in step (h) comprises methanation.

5. Process of claim 1, wherein the purifying of the gas effluent in step (h) comprises a cryogenic process.

6. Process of claim 1, wherein the electrolysis of water in step (b) is powered by renewable energy.

* * * * *